United States Patent
Banerjee et al.

[11] Patent Number: 5,454,716
[45] Date of Patent: Oct. 3, 1995

[54] AESTHETIC ORTHODONTIC ARCH WIRE

[75] Inventors: Satyajit Banerjee, Pasadena; Jerold S. Horn, Granada Hills; Robert P. Eckert, Alta Loma, all of Calif.

[73] Assignee: Minnesota Mining and Manufacturing Co., St. Paul, Minn.

[21] Appl. No.: 613,958

[22] Filed: Nov. 15, 1990

Related U.S. Application Data

[63] Continuation of Ser. No. 180,289, Apr. 11, 1988, abandoned.

[51] Int. Cl.$^6$ ........................................................ A61C 3/00
[52] U.S. Cl. ........................................................ 433/20
[58] Field of Search ................................................ 433/20

[56] References Cited

U.S. PATENT DOCUMENTS

| | | | |
|---|---|---|---|
| Re. 30,332 | 7/1980 | Wallshein | 433/20 |
| Re. 30,593 | 4/1981 | Wallshein | 433/20 |
| 3,504,438 | 4/1970 | Wittman et al. | 32/14 |
| 3,545,083 | 12/1970 | Krasne | 32/5 |
| 3,988,832 | 11/1976 | Wallshein | 32/14 A |
| 4,050,156 | 9/1977 | Chasanoff et al. | 32/2 |
| 4,120,090 | 10/1978 | Kesling | 32/14 A |
| 4,364,731 | 12/1982 | Norling et al. | 433/218 |
| 4,412,819 | 11/1983 | Cannon | 433/20 |
| 4,479,779 | 10/1984 | Wool | 433/20 |
| 4,568,558 | 2/1986 | Angrick et al. | 427/2 |
| 4,585,414 | 4/1986 | Kottemann | 433/20 |
| 4,650,550 | 3/1987 | Milnes et al. | 204/38.7 |
| 4,659,310 | 4/1987 | Kottemann | 433/20 |
| 4,731,018 | 3/1988 | Adell | 433/20 |
| 4,869,666 | 9/1989 | Talass | 433/20 |

FOREIGN PATENT DOCUMENTS

| | | |
|---|---|---|
| 1001457 | 12/1976 | Canada. |
| 0142172 | 5/1985 | European Pat. Off.. |

OTHER PUBLICATIONS

"Tooth–Colored Ortho Wire", *Dental Products Report*, Apr. 1988, 22, #4, p. 124.

*Primary Examiner*—Nicholas D. Lucchesi
*Attorney, Agent, or Firm*—Morton J. Rosenberg; David I. Klein

[57] ABSTRACT

An orthodontic arch wire comprises a wire having the same dimensions as previously used orthodontic arch wires. The wire is coated with an opaque coating of a composite material having a thickness of no more than 35 microns, and preferably less than 12 microns. The composite material comprises a resin binder loaded with filler particles for strengthening the coating and making it approximately tooth colored. The composite coating is sufficiently adherent to the arch wire for bending from a straight wire to a curved arch wire installed in a patient's mouth while retaining the aesthetic coating, and to prevent stripping as the arch wire moves through the arch wire slot in an orthodontic bracket.

11 Claims, 2 Drawing Sheets

AESTHETIC ORTHODONTIC ARCH WIRE

This is a continuation of application Ser. No. 07/180,289 filed on 11 Apr. 1988, now abandoned.

BACKGROUND OF THE INVENTION

This invention relates to metal arch wires used for orthodontic correction of teeth wherein the wires are coated to have a color blending aesthetically with that of teeth.

Orthodontic treatment of improperly positioned teeth involves the application of mechanical forces to urge the teeth into correct alignment. The most common form of treatment uses orthodontic brackets which are small slotted bodies configured for direct cemented attachment to the front (labial) or rear (lingual) surfaces of the teeth, or alternatively for attachment to metal bands which are in turn cemented or otherwise secured around the teeth.

A resilient curved arch wire is then seated in the bracket slots. The restoring force exerted by the bent and twisted resilient wire tends to shift the teeth into orthodontically correct alignment. Depending on the shape of the arch wire (both round and rectangular cross sections are in common use) and the orientation of the bracket slot, it is possible to apply forces which will shift, rotate or tip the teeth in any desired direction.

Stainless steel is in many ways an ideal material for orthodontic brackets and wires because this metal is strong, nonabsorbent, weldable, and relatively easy to form and machine. Arch wires are also made of nickel-titanium alloys with a "shape memory" highly desirable in initial stages of orthodontic correction. A significant drawback of metal appliances, however, relates to cosmetic appearance when the patient smiles. Adults and older children undergoing orthodontic treatment are often embarrassed by the "metallic smile" appearance of metal brackets and wires, and this problem has led to various improvements in recent years.

One relates to development of adhesives, bracket bases, and techniques for direct cemented attachment of brackets to at least the anterior teeth which are prominently displayed when smiling. Direct cementation eliminates the need for metal tooth bands which are a major factor in the metallic-smile problem. Part of this has included development of smaller brackets which are less obtrusive.

Still another area of improvement involves use of non-metallic materials for the brackets. Ceramic orthodontic brackets have now been developed which are translucent and assume the color of underlying teeth so as to minimize appearance of metal in the mouth. The ceramic materials present a significantly improved appearance in the mouth, and often the only visible metal component is the arch wire. It is desirable to eliminate this last remaining metallic appearance from the anterior teeth.

It seems certain that metal wire will remain the material of choice for orthodontic arch wires because of its strength, stiffness and ductility. Thus, rather than a change of material, it appears that a coating to camouflage the metal is the only practical way of providing an aesthetic orthodontic arch wire. Wires have been coated with various non-metallic materials since at least as early as experiments with electromagnets and transformers. A variety of materials have been used for coating wires, but available coated wires are unsatisfactory for a commercially acceptable orthodontic arch wire. There are significant constraints on the properties of materials suitable for orthodontic use addressed in practice of this invention.

Plastic coating of orthodontic arch wires has previously been suggested. For example, U.S. Pat. No. 3,504,438 by Wittman et al. proposes replacing prior porcelain and acrylic coating materials for orthodontic devices with polytetrafluoroethylene (Teflon) or a material having similar properties such as fluorinated ethylenepropylene (Teflon FEP), trifluorochloroethylene, vinylidene fluoride, polyphenylene oxide, nylon, irradiated modified polyolefins and polycarbonates and other organic and inorganic polymeric materials (column 3, lines 32 to 38). It is stated to be desirable that the coating be colored similarly to the teeth and be characterized by the zero coefficient of friction of the Teflon. The Teflon is applied to a bracket, for example, by stretching and heat shrinking a Teflon sleeve. Spraying or dipping for the orthodontic devices is also contemplated. The thickness of the coating is unstated.

U.S. Pat. No. 4,050,156 by Chasanoff et al. describes an orthodontic arch wire coated with a layer of a mixture of para-oxybenzoyl homopolyester and polytetrafluoroethylene. This plastic may use titanium dioxide as a pigment. The thickness of the coating is not stated. The properties of the coating are said to be enhanced by the high content of thermoplastic fluorocarbon. In what may be a reference to the subject matter of the Wittman patent, the Chasanoff patent states that acrylics, porcelains and pure Teflon (polytetrafluoroethylene) coatings have been attempted, but have drawbacks such as lack of abrasion resistance, lack of stength, brittleness, and propensity to staining. It is not known that the product described in the Chasanoff patent has been commercially viable.

U.S. Pat. Nos. 4,585,414 and 4,659,310 by Kottemann describe an orthodontic arch wire in the form of an extruded plastic rod reinforced with a stainless steel wire core. It is stated that the stainless steel wire has a diameter in the range of from 0.008 inches to 0.014 inches, and after coextrusion with a plastic coating, the resulting product has an outside diameter in the range of from 0.016 inches to 0.022 inches. Thus, the thickness of the plastic is in the order of 0.004 inch (100 microns or micrometers). The '310 patent has an example where the wire core has a diameter of 0.011 inch and the total arch wire has a cross section of 0.018 inch yielding a plastic thickness of 0.0035 inch (89 microns).

The plastics employed comprise polysulfone and polyetherimide resins. It is conceded in the Kottemann patent that the resultant product is 27 times more flexible than stainless steel and 7 times more flexible than Nitinol. This, of course, means that much less corrective force can be applied to the patient's teeth due to the decreased properties of the arch wire. A product which is apparently similar to the product described in the patents is marketed by American Ortho under the trademark Filaflex.

U.S. Pat. No. 3,988,832 by Wallshein describes an orthodontic arch wire made in the form of a tightly wound helix of metal. It is stated that a soft coating may be placed on the exterior of the helix to protect the tissues in the mouth from the wire, as well as to prevent food particles from entering into the spaces in the wire. A plasticized and elastic material is used so as not to substantially affect the flexibility or working range of the arch wire. The thickness of the coating is not mentioned.

Prior soft, thick, thermoplastic coatings have not been satisfactory for appreciable use in orthodontics. As has been suggested, the required thickness of coating has reduced the stiffness of the wires and their suitability for orthodontic correction. A significant difficulty with prior attempts to coat orthodontic arch wires with plastics has been stripping of the plastic from the wire. During the course of orthodontic correction, the arch wire moves through the arch wire slot in the bracket attached to a tooth. This may occur during adjustment or correction. Such movement along the arch wire slot tends to strip the coating from the wire, much as one would strip wire for making an electrical connection. Small shreds of plastic coating are removed from the arch wire. Further, thick coatings tend to buckle on the inside of a bend in the arch wire, and that may be a location for failure of the coating.

It has also been proposed to apply an aesthetically appearing coating on just the "front" face of an arch wire. This enables the wire to have a full cross section for fitting in the arch wire slot of conventional brackets. A variation of this idea is described in U.S. Pat. No. 4,731,018 by Adell. The Adell patent describes a metal wire with a non-round cross section with a non-metallic part completing the circular cross section. Rectangular cross sections are also described.

Any such coating that extends around less than the full perimeter of the arch wire must have outstanding adhesion to the wire to prevent flaking or peeling. Further, with round arch wire, application of such a coating in a continuous process makes it difficult to assure that the coating is uniformly placed on the front face of the arch wire.

It is desirable to provide an aesthetically pleasing orthodontic arch wire overcoming such deficiencies in the prior art.

BRIEF SUMMARY OF THE INVENTION

There is, therefore, provided in practice of this invention according to a presently preferred embodiment, an aesthetic orthodontic arch wire where the metal wire has sufficient strength, stiffness, and transverse cross section for applying orthodontic correction forces to a patient's teeth. The wire is coated with a composite material having a thickness of no more than 35 microns. The composite material comprises a resin binder and sufficient filler particles distributed in the binder to make the coating substantially opaque. A multi-layer coating having a layer of transparent resin may also be employed. Preferably the resin is curable by exposure to ultraviolet radiation, an electron beam, or elevated temperature so that there can be continuous coating of the wire before the wires are formed to the desired arch shape.

BRIEF DESCRIPTION OF THE DRAWINGS

These and other features and advantages of the present invention will be better understood by reference to the following detailed description when considered in connection with the accompanying drawings wherein.

DETAILED DESCRIPTION

Figure 1:
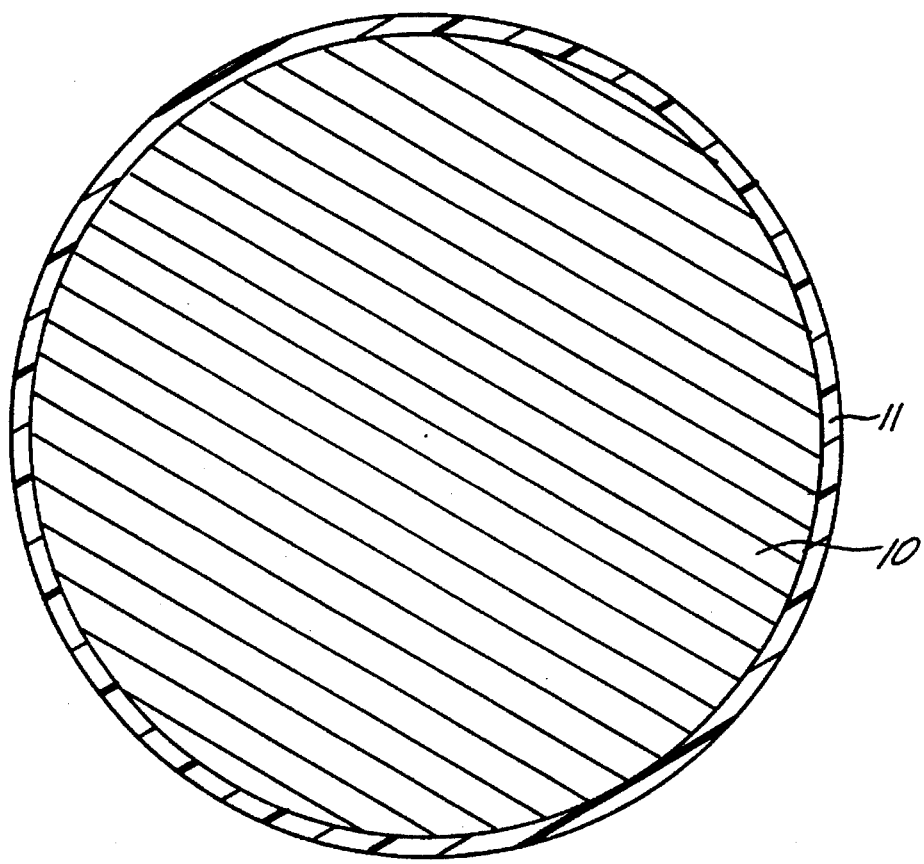
FIG. 1 is a transverse cross section of an exemplary round aesthetic orthodontic arch wire constructed according to principles of this invention.

Brackets for making orthodontic corrections are commercially available with two different widths of arch wire slots 18 mils (0.46 mm) and 22 mils (0.56 mm). Either round or rectangular arch wires are used in eleven standard sizes. Conventional arch wires have diameters of 0.36 mm, 0.41 mm, 0.56 mm, and 0.51 mm. Exemplary rectangular wires range from 0.41×0.46 mm, to 0.53×0.63 mm. Square wires of 0.41 and 0.46 mm are also used.

It has been found quite important to employ a thickness of coating on a metal arch wire no more than 35 microns (micrometers) thick and preferably no more than 12 microns thick. With such a thin coating standard size arch wires can continue to be used with standard brackets to produce nearly the same corrective forces presently available. The coating is sufficiently thin that it does not interfere with passage of the arch wire through the arch wire slot in such a bracket.

Further, a coating that is thin relative to the thickness of the wire on which it is placed, that is, less than 7% of the wire diameter, is also advantageous in that when sharp bends are made in the arch wire as must often be done in orthodontic work, even a hard, rigid coating can remain intact on the bent wire without buckling and flaking on the inside of a bend or cracking and peeling on the outside of a bend. Preferably the thickness of the coating on the arch wire is less than 4% of the arch wire cross section. The thin coating is sufficiently flexible and adherent to the wire that it does not crack, split or flake when the wire is bent around itself. That is, the wire is twisted around a wire of the same diameter as a measure of the resistance of the coating to cracking or splitting.

With such a thin coating, the properties of the coating material are significant. Not only must the coating not crack, chip or peel while the orthodontist performs the manipulation of the wire to set and adjust the braces, but it must also be able to withstand without cracking, chipping or peeling, the physical beating to which a typical teenage patient subjects the braces during orthodontic treatment. Although an arch wire may be left in a patient's mouth for as much as six months, a more typical application leaves a given arch wire in place for up to four months. Not only must the arch wire coating withstand abuse for such a period, but also it must remain biocompatible and have no appreciable corrosion in the environment of the mouth.

To achieve the desired aesthetic characteristic, the coating is opaque so that the metal does not show. It is not only opaque, it has a color blending with that of the teeth to be less conspicuous. Further, during the residence of the arch wire in the patient's mouth, the coating is substantially unstained by the various foods and beverages ingested.

The coating is also sufficiently abrasion resistant to remain substantially opaque and continuous for at least four months in the patient's mouth. It will be recognized that under some conditions abrasion of portions of the arch wire may wear through limited areas of the coating. This is not a severe problem since minor metallic areas are relatively inconspicuous. Such wear occurs gradually through the coating and the edges of the coating around such worn areas become feathered for minimizing the conspicuousness of any bare areas on the arch wire.

Further, the coating is sufficiently adherent to the wire and strong enough to avoid stripping as the arch wire moves through the arch wire slot on brackets. It will be recognized that some wear may occur since the coating is necessarily softer than aluminum oxide or the like used for making ceramic brackets. The smooth surface of the coating, its tight adhesion to the wire, and the mechanical support acquired from the wire by reason of the small thickness of the coating, tend to minimize damage from this cause.

Stain resistance of the coating is significant in the context of an aesthetic orthodontic arch wire. It is undesirable to have food stains or the like significantly discolor the arch wire while it resides in the patient's mouth.

Stain resistance of products of this nature are evaluated by exposure to food and beverage substances which have been found to have a high propensity for staining. Exemplary materials which have been found to stain various materials include mustard, cranberry juice, coffee, soy sauce, and ketchup. Stain resistance of an arch wire coating is evaluated by immersing the coated arch wire in such materials for a period of 24 hours and comparing the color of the tested coating to that of a coating that has not been immersed. Suitable coatings do not show any significant staining after 24 hours of immersion in mustard, coffee, cranberry juice or soy sauce.

In an exemplary embodiment, the arch wire 10 is surrounded by a layer 11 of a composite material formed of a resin binder and a opacifying filler. The filler comprises sufficient particles distributed in the resin binder to make the coating substantially opaque. It is preferred to employ a hard ceramic for the filler since ceramic particles also impart abrasion resistance, hardness and strength to the coating.

Resins suitable for use in practice of this invention include acrylics, epoxies, liquid crystal polymers, acetals, nylons, polysulfones, polyamides, polyimides, polyacetates, phenolics, polyesters, and amino type resins such as melamine formaldehyde, and urea formaldehyde.

The resin binder is preferably a thermoset resin or a high melting point liquid crystal polymer. Such materials have the strength, adhesion, hardness, abrasion resistance and resistance to staining to be satisfactory for the thin coatings provided in practice of this invention.

Particularly preferred resins include polyacrylates (including methacrylates and the like) epoxies such as bisphenol A-epichlorohydrin and polyphenyl sulfone polymers which are ultraviolet, electron beam, or heat curable. The heat curing acrylics and epoxies are particularly preferred for rapid, continuous processing. In such an embodiment an acrylic monomer, or mixture of monomers and oligomers with a suitable catalyst is applied to the surface of the wire and cured in place to form a coating. The curing occurs as the wire is run through a heating oven, typically a tower where the wire may make several passes through to reside at elevated temperature a sufficient time for a complete cure. Thermoset resins are particularly preferred so that they remain solid during subsequent heat treatment of some types of arch wires.

Resins employed in practice of this invention include acrylates and modified acrylates which cross link for forming thermoset compositions, preferably by heating, or by irradiation by ultraviolet or an electron beam. One can use, for example, 2-aminoethylmethacrylate which provides excellent adhesion to a primed substrate, and the ortho hydrogen of the amine group may also act as a co-initiator of ultraviolet polymerization with an ultraviolet absorber such as benzophenone or the like. Additional polyfunctional acrylates are employed for cross linking and hardening the cured polymer.

Examples of suitable mono and multifunctional acrylates include 2-phenoxyethyl acrylate, isobornyl acrylate, bisphenol-A glycidyl methacrylate, cyclohexyl acrylate, polyethylene glycol dimethacrylate, 1,6-hexanediol diacrylate, tripropylene glycol diacrylate, trimethylol propane triacrylate, and the like. Various cross linkers such as divinyl or polyvinyl compounds such as divinyl benzene, N,N'-methylene-bis-acrylamide, allyl diglycol carbonate or the like may also be included.

For ultraviolet or electron beam curing, a free radical producing photoinitiator for acrylate resin is also incorporated in the coating, typically in a concentration of about 5% based on the weight of solids in the composition. Examples of ultraviolet photoinitiators include benzophenone, acetophenone, dimethoxy phenol acetophenone, benzil, benzil methyl ketone, benzoin methyl ether, benzoin isopropyl ether, phenyl glyoxal, and the like. The photoinitiator may also include a synergistic agent such as a tertiary amine to enhance conversion of absorbed energy to polymerization initiating free radicals.

Suitable photoinitiators also include carbonyl compounds such as diacetyl; organic sulfur compounds such as alkyl disulfides, aryl disulfides, aroyl disulfides, acyl disulfides, cycloalkyl disulfides, and mercaptans; peroxides and hydroperoxides; redox systems such as hydrogen peroxide-ferrous ion; azo and diazo compounds; certain halogen compounds such as 1-chloromethyl naphthalene and phenyl bromide; and the like.

Complete cross linking of the acrylate is desirable. Thus, a slight excess of photoinitiator may be employed in the composition to assure sufficient free radical formation to promote complete polymerization. It is, therefore, desirable that the photoinitiator and its decomposition products be biocompatible and not release any toxic substances in the environment of the mouth.

Epoxy resins are also particularly desirable for practice of this invention. In particular, bisphenol A epoxy resin curable at temperatures less than 230° C. and preferably no more than 200° C. are preferred. The lower temperature coating and curing techniques are preferred so that the same resin system may be used on stainless steel, titanium or nickel-titanium alloy arch wires. This is desirable since nickel-titanium alloys are advantageous materials for use in orthodontic arch wires because of their so-called shape memory and pseudo-elasticity. These alloys have their memory set to the desired shape by heat treatment. Depending on the alloys heat treatment may range from less than 300° C. up to 450° C.

It is desirable to coat the arch wire with the aesthetic coating in a continuous process before the individual arch wires are shaped since this enhances the uniformity of the coating on the wire and is more economical than coating individual arches after they are shaped and cut. Thus, it is desirable that the resin be applied and cured at a lower temperature than the temperature at which the nickel-titanium alloy is heat treated, so that continuous coating may be employed without interfering with subsequent heat treatment. Further, it is desirable that the resin have a thermal degradation temperature less than the heat treatment temperature, and that it be thermoset so that the thickness of the coating remains intact as the arch is formed and heat treated. Such considerations are not directly applicable for stainless steel wire, but it is preferred to employ the same coating composition for stainless steel, titanium and nickel-titanium alloys.

Liquid crystal polymers suitable for use in practice of this invention include aromatic co-polyester thermoplastics. Such materials exhibit a highly ordered structure in both the liquid and solid states. Although thermoplastic, they can be suitable since the softening temperatures are quite high and the materials have suitable mechanical properties for forming a thin, strong and adherent coating for arch wires. Liquid crystal polymer resins are available under the trademarks Xydar from Dartco Manufacturing Co., Augusta, Ga.; Vectra from Hoechst Celanese, Chatham, N.J.; and HTR from Granmont, Inc., Granville, Ohio. Other high temperature engineering thermoplastics such as polyethersulfone and polyetheretherketone may also be used.

In a preferred embodiment, the filler for the resin binder comprises titanium dioxide. If desired up to about 20% of the filler can be aluminum oxide. Suitable fillers also include aluminum oxide, zirconium oxide, silicon dioxide and boron nitride. Silica may be included in the form of glass microspheres, such as for example, chemically stable, soda-lime/borosilicate glass microspheres. The filler is present in the resin in the range of from 2% to 40% by weight. It is also significant that the particle size of the filler be small since the coating is quite thin. The particle size is less than one micron, and preferably no more than one half micron.

Figure 2:
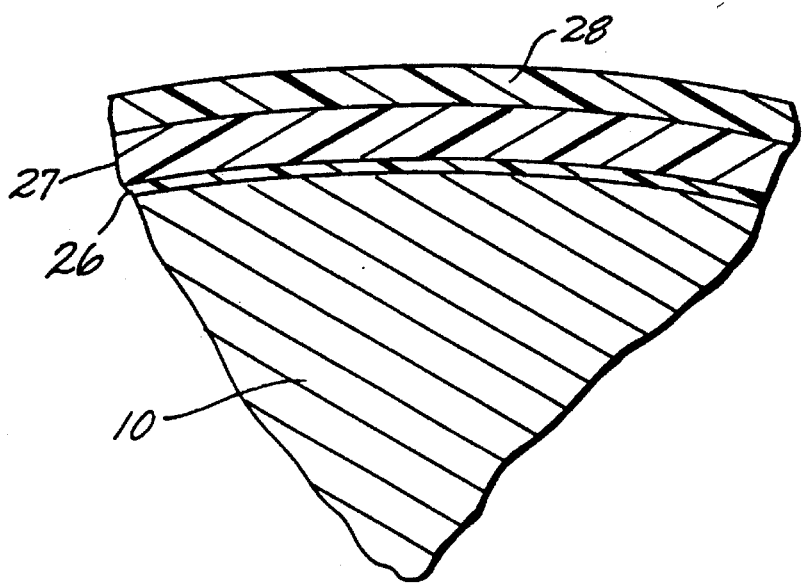
FIG. 2 is an enlarged fragmentary cross section of an exemplary aesthetic orthodontic arch wire.

As illustrated in FIG. 2, an organo-metallic coupling agent layer 26 is first applied to the surface of the wire for promoting adhesion. The coupling agent layer is essentially one molecule thick; hence is illustrated in exaggerated thickness in the schematic cross section of FIG. 2. In effect, the coupling agent layer changes the characteristics of the surface from the inorganic metal to the organic moiety of the organo-metallic coupling agent.

The organic group of the organo-metallic coupling agent interacts with the organic resin in the composite coating to give greater adhesion between the resin and the organo-metallic coupling agent than is typically possible between the resin and the metal, absent such treatment. Often polymerization between the organic resin and the non-hydrolyzable organic group of the organo-metallic coupling agent will provide the strongest bonds; for example, an organo-metallic coupling agent having a methacryl group can polymerize with a methacrylate resin and gives particularly strong bonding.

Preferred coupling agents are silanes. A broad variety of organofunctional silanes are commercially available as coupling agents. Broadly speaking, the organosilanes have one to three hydrolyzable moieties and three to one non-hydrolyzable organic groups on a silicon atom. Most commonly the hydrolyzable moieties comprise chlorine, a siloxy group or an alkoxy group. Alkoxy groups are preferred in practice of this invention since the hydrolysis products are alcohols. A broad variety of organic groups may be included on the silane molecule to provide desired properties of the coupling agent.

A particularly preferred organofunctional silane for use with an acrylic resin coating comprises gamma-methacryloxypropyltrimethoxy silane. This material is available from Union Carbide Corporation under their designation A-174, from Dow Corning Corporation under their designation Z6030, from Petrarch Systems Silanes and Silicones, Bristol, Pa., under their designation M8550, or from PCR Research Chemicals, Inc., under their designation 29670-7. Exemplary silane coupling agents from the many available include:
3-(2-Aminoethylamino)propyltrimethoxy silane
3-Chloropropyltrichloro silane
3-Chloropropyltrimethoxy silane
Vinyltriacetoxy silane
Vinyl-tris(2-methoxyethoxy) silane
Beta-3,(4-epoxycyclohexyl)ethyltrimethoxy silane
Gamma-mercaptopropyltrimethoxy silane
Gamma-aminopropyltriethoxy silane
Aminoalkyl silanes such as gamma-aminopropyltriethoxy silane, gamma-aminopropyltrimethoxy silane, N-beta-(aminoethyl)-ethyl)-gamma-aminopropyltrimethoxy silane and N'-(beta-aminoethyl)-N-(beta-aminoethyl)-gamma-aminopropyltrimethoxy silane may be used for a broad variety of resins including phenolics, vinyls, polyurethanes, epoxies and acrylics.

Mercaptoalkyl silane coupling agents may be used with epoxy resins or polysulfides. Exemplary materials include gamma-mercaptopropyltrimethoxy silane and gamma-mercaptopropyltriethoxy silane. Silanes having vinyl groups are suitable as "primers" for polyesters. Exemplary vinyl silane coupling agents include vinyl-trichloro silane, vinyltriethoxy silane, vinyl-trimethoxy silane, vinyltris-(beta-methoxyethoxy) silane and vinyltriacetoxysilane. If desired, one may use gamma-ureidoalkyltriethoxy silane for compatibility with urea formaldehyde resins.

The silane coupling agents are deposited on the metal surface in a conventional manner. They may be applied without hydrolysis or may be prehydrolyzed before application to the substrate. Typically they are deposited from a solvent solution and cured in place on the substrate. Condensation occurs in the prehydrolyzed silane coupling agent or, if not prehydrolyzed, adventitious water promotes polymerization. Heating of the silanated surface can accelerate curing. Other organometallic coupling agents besides silanes are suitable, including for example, zirconates, titanates and aluminates.

Adhesion to the substrate can also be enhanced by roughening the substrate for increasing its "tooth". Roughening can be provided by grit blasting or etching the wire before silanation.

After application of the silane coupling layer 26, a layer 27 of composite resin and filler particles is applied. Such a composite resin comprises, for example, a modified acrylic resin containing particles of titanium dioxide, for providing strength and opacity to the coating. A small amount of black or gray pigment, such as carbon, is included for changing the color of the coating from the stark white of titanium dioxide to a gray tone which better camouflages the arch wire in front of a patient's teeth. Surprisingly, a light gray tone has been found to be less obtrusive than a slightly yellow or brown tint as is commonly found in teeth.

If desired, a final layer of finishing varnish 28 can be applied over the composite coating for providing a hard, smooth surface. Commercially available modified acrylic varnishes such as C1225-98A or 34W13 available from BASF Corporation, Cincinnati, Ohio, or a cycloaliphatic epoxide enamel such as 43R3 from BASF Corporation may be employed as a transparent finishing coat over the loaded composite resin layer.

In another embodiment a thin coating of unloaded resin, i.e., resin without ceramic filler, may be first applied over the silanation layer and exposed to elevated temperature, ultraviolet or an electron beam for initiating a cure before applying a composite coating layer loaded with ceramic particles. This tends to minimize difficulty in curing of the resin adjacent to the substrate, thereby enhancing adhesion of the coating to the substrate.

Figure 3:
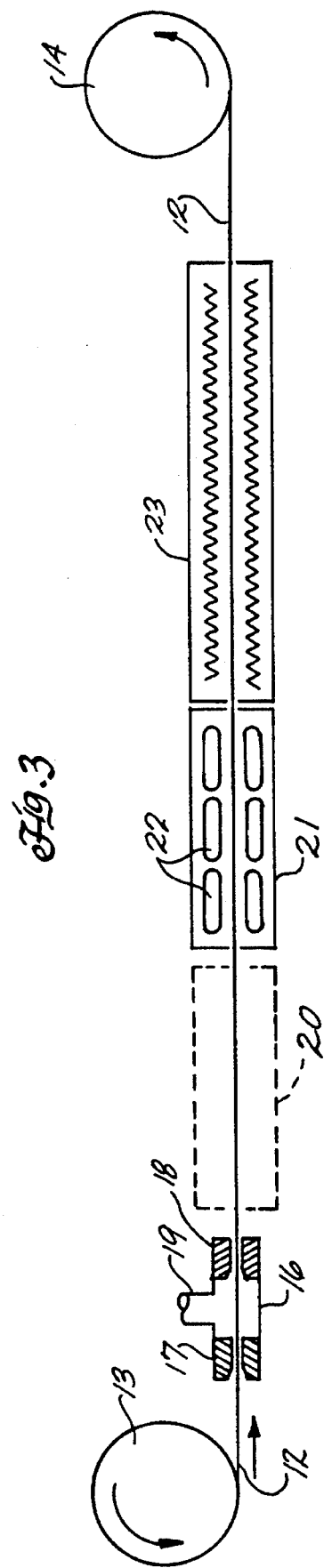
FIG. 3 is a schematic illustration of an exemplary wire coating technique.

An exemplary wire coating facility is illustrated schematically in FIG. 3. Silanated wire 12 is unrolled from a spool 13, passed through the coating apparatus, and is wound on a take-up spool 14. In the illustrated arrangement the wire passes through a coating chamber 16 which is kept filled with a suitable resin by way of a filler tube 19. The wire enters the chamber through a suitable orifice such as a drill bushing 17. The entrance orifice is larger than the diameter of the wire a sufficient amount to permit clear passage, yet prevent the leakage of appreciable amounts of uncured resin from the coating chamber.

The exit orifice may also comprise a drill bushing 18 having a diameter sufficiently larger than the wire diameter for controlling a coating with a desired thickness. For example, a wire having a diameter of 0.41 mm is drawn through an orifice having a diameter of 0.46 mm. After curing the resultant coating which shrinks some in the process, the coated wire has a diameter of 0.427 mm. Thus, a coating thickness of 8.5 microns, or only about 2% of the wire diameter can be obtained.

A uniform thickness coating is obtained on the wire because, with the relatively viscous resin mixture applied and the small clearance between the orifice and wire, a hydrodynamic bearing is formed which reliably centers the wire in the orifice as it is drawn.

From the coating station the wire optionally passes through a drying station 20. This may be of significance where a volatile solvent is employed for reducing viscosity of the liquid resin. The drying station removes such solvents before curing the resin. In the absence of solvent, such a drying station may be omitted. The drying can be by way of circulating gas such as air, or, if desired, an inert gas such as nitrogen. With an ultraviolet curable acrylic, it may be desirable to employ nitrogen since oxygen tends to inhibit curing. Heat may also be applied in the drying station to expedite solvent removal and assure that there is no condensation of water following evaporative cooling by solvent removal.

From the drying station, if employed, the wire passes directly to a heating chamber, or if a radiation curable resin is used, through an ultraviolet exposure chamber 21. Such a chamber is fitted with conventional ultraviolet lamps 22 for irradiating the coating as it passes through the chamber. The number and intensity of the lamps in the chamber and the residence time of the wire in the ultraviolet chamber are chosen to effect substantial curing of the resin in the coating.

The ultraviolet is absorbed by a photoinitiator in the resin mixture to stimulate a reaction which creates free radicals for polymerization of the resin. After reaction of the photoinitiator, it no longer absorbs ultraviolet to the same extent. Thus, curing progresses from the outer surface through the bulk of the thickness of the layer and finally to the interface between the wire and resin. It is important to have sufficient irradiation to cure resin adjacent to the wire since this promotes adhesion of the resin to the wire.

The presence of filler particles in the resin tends to interfere with deep curing of the resin by preventing transmission of the ultraviolet. Thus, the same pigments that provide the aesthetic effect by making the coating opaque also tend to make it opaque to the ultraviolet used for curing. The residence time in the ultraviolet radiation is sufficient to release free radicals throughout the thickness of the coating before the wire leaves the ultraviolet irradiation station.

From the UV chamber, or directly after coating in the event the resin is heat curable, the wire passes through a heating tunnel 23 which raises the temperature of the wire and coating to about 200° C., for example, for promoting a full cure of the resin before the wire reaches the take-up spool. The temperature, of course, depends on the resin employed. A full cure is not required before the take-up spool when there has been adequate irradiation and sufficient cure to form a rigid coating. The curing tends to proceed after photoinitiation, and polymerization may continue for several hours to develop the final properties of the coating.

As will be apparent, there are many possible variations in such a wire coating line. For example, as pointed out herein, the coating layer may actually comprise a plurality of layers. These may be partially cured between application of the first and second layers, or resins that are immiscible may be used for successive layers which are cured simultaneously. Different curing regimens may be employed for each of such layers. Resin blends suitable for photoinitiation with visible light are also usable. Further, instead of ultraviolet, the coating may be irradiated with an electron beam for deeper penetration into a coating having a high proportion of ceramic filler. If a thermoplastic resin is applied at elevated temperature, curing is not required.

It is preferred to employ heating alone for curing the coating. Various epoxy and acrylic resins may be employed for which exposure to elevated temperature alone is sufficient to promote polymerization. This is preferable since the processing is simpler, and can proceed rapidly and safely with conventional equipment.

Other techniques for calendering a desired coating thickness on the wire may be employed. Spraying, wiping electrostatic or electrolytic coating, and coextrusion are also suitable. Thus, it will be apparent that specific details of the coating and curing line are to some extent dependent on the coatings employed.

It will be noted that variations of preferred coatings for providing aesthetic orthodontic arch wires have been set forth hereinabove. It will, therefore, be recognized by those skilled in the art that many modifications and variations may be feasible in practice of this invention. It is, therefore, to be understood that within the scope of the appended claims the invention may be practiced otherwise than as specifically described.

What is claimed is:

1. An orthodontic wire comprising:

a metal wire, a layer of tooth color material covering said metal wire to present a color simulating that of teeth with which the orthodontic wire is adapted to be used, and a layer of clear material covering said tooth color layer to protect said layer of tooth color material in an intra-oral environment while allowing the color of the layer of tooth color material to be presented through the layer of clear material.

2. An aesthetic orthodontic arch wire comprising:

a metal wire having sufficient strength, stiffness and transverse cross section for applying orthodontic correction forces to a patient's teeth; and an abrasion resistant coating formed on the wire having a thickness of no more than 12 microns, the coating comprising a composite material having a resin binder and sufficient filler particles distributed in the resin binder to make the coating substantially opaque, said coating comprising ceramic particles having a particle size no more than one half micron, whereby said ceramic particles impart abrasion resistance, hardness and strength to said coating of said wire.

3. An aesthetic orthodontic arch wire as recited in claim 2 wherein the resin is selected from the group consisting of acrylic resins, epoxy resins, and liquid crystal polymers.

4. An aesthetic orthodontic arch wire as recited in claim 2 wherein the particles are selected from the group consisting of titanium dioxide, aluminum oxide, zirconium oxide, silicon dioxide, boron nitride, and glass.

5. An aesthetic orthodontic arch wire as recited in claim 4 wherein the particles comprise a sufficient amount of black or gray pigment for blending with appearance of a patient's teeth.

6. An aesthetic orthodontic arch wire as recited in claim 2 wherein the coating comprises two layers, the layer of composite material, and a second layer of thermoset resin without pigment.

7. An aesthetic orthodontic arch wire as recited in claim 6 wherein the second layer is between the composite layer and the wire.

8. An aesthetic orthodontic arch wire as recited in claim 6 wherein the second layer is outside of the composite layer.

9. An aesthetic orthodontic arch wire as recited in claim 2 further comprising a layer of organo-metallic coupling agent between the wire and the coating.

10. An aesthetic orthodontic arch wire as recited in claim 2 wherein said coating has a proportion of said particles in the range of from 2 to 40 percent by weight.

11. An aesthetic orthodontic arch wire as recited in claim 2 wherein the resin binder is a thermoset resin curable by elevated temperature, or by exposure to ultraviolet radiation or an electron beam.

* * * * *